United States Patent [19]

Roberts

[11] Patent Number: 4,754,786

[45] Date of Patent: Jul. 5, 1988

[54] STERILE FLUID STORAGE AND DISPENSING APPARATUS AND METHOD FOR FILLING SAME

[76] Inventor: Roderick Roberts, 23652 Via Ortega, Trabuco Canyon, Calif. 92679

[21] Appl. No.: 904,348

[22] Filed: Sep. 5, 1986

[51] Int. Cl.⁴ .............................................. B65B 3/04
[52] U.S. Cl. ...................................... 141/1; 141/244; 141/383; 141/286; 604/52; 210/257.1; 222/482
[58] Field of Search ................... 141/234–248, 141/10, 67, 68, 114, 313–317, 383–386, 285–310, 19, 329, 330, 382, 1–9, 11, 12; 604/411, 412, 413, 414, 415, 416, 52; 210/257.1, 257.2; 222/482

[56] References Cited

U.S. PATENT DOCUMENTS

| 1,659,384 | 2/1928 | Thomas | 141/244 |
| 3,246,674 | 4/1966 | Kapeker | 141/383 |
| 4,607,671 | 8/1986 | Aalto et al. | 141/383 |

Primary Examiner—Houston S. Bell, Jr.
Attorney, Agent, or Firm—Price, Gess & Ubell

[57] ABSTRACT

A disposable apparatus for sterilizing fluid and dispensing it includes a bag, a filter element, a conduit element, and a plurality of dispensing elements serially communicating with each other for providing a sterile fluid dispensing path that can be serially opened and closed. Methods are also provided for filling such apparatus in conjunction with a closed environment of an assembly having at least one mixing vessel, a reservoir container, a filling area, a filter element, and a plurality of storage elements interfacing the filling area.

11 Claims, 2 Drawing Sheets

STERILE FLUID STORAGE AND DISPENSING APPARATUS AND METHOD FOR FILLING SAME

BACKGROUND OF THE INVENTION

1. Field of the Invention

The present invention relates generally to sterile fluid containers and methods for sterile filling them and, specifically, to an improved disposable apparatus that can store and dispense a fluid while maintaining the sterility of it and methods for filling such apparatus in a sterile manner.

2. Brief Description of the Prior Art

A continuing problem that has plagued the medical and pharmaceutical industries has been that of maintaining sterility (absence of bacteria) in manufacturing, storing, and dispensing fluids, such as blood serum, tissue culture media, and intravenous solutions. With the increased awareness of transmitting diseases, such as Acquired Immune Deficiency Syndrome (AIDS), has come an increased awareness for not only maintaining the sterility of the fluid itself but also taking precautionary measures to prevent the transmission of diseases through the apparatus used in conjunction with such fluids.

Attempts have been made in the past to address some of the above problems. For example, Silbert, "Method and Apparatus for Sterile Handling of Fluids," U.S. Pat. No. 4,058,363 discloses a semi-circular shaped manifold assembly having a plurality of openings. The manifold is connected to a fluid container having a fluid therein which is to be handled in a sterile fashion. The manifold is further connected to a sterilizing solution container having a sterilizing solution that is introduced into the manifold assembly to sterilize all of the connections therein. One drawback to such a manifold is the necessity of having to always flush the manifold with a sterilizing solution which may or may not be effective on a particular flushing.

Another example in which artistans have attempted to address some of the problems mentioned above s Kirschner, "Means for Sterilely Transferring Blood Plasma, Serum, Biological or Pharmaceutical Fluids, and the Like," U.S. Pat. No. 3,566,930. Kirschner describes a flat elongated manifold member having a plurality of branch conduits, and check valves disposed at the juncture of each branch conduit with the manifold to regulate the flow of fluid between a plurality of storage containers and a larger pooling container. While Kirschner provides a degree of disposability, apart from the pooling container, the apparatus does not appear to be readily adaptable for integration into a continuous process for manufacturing the sterile fluid and then dispensing it. Thus, whatever sterility is maintained from the transfer of fluid from the storage containers to the pooling container is effectively lost if the sterility is not continuously maintained between the fluid source and storage containers.

Industrial processes utilize a clean room. In the clean room, receiving containers move pass a fluid dispenser in assembly line fashion to be filled with a quantity of the fluid. The containers are then sealed. This has the disadvantage of requiring a large, expensive clean room and allows for the possibility of contamination of the fluid during dispensing and then sealing.

A need therefore exists in the art to provide a apparatus that can sterilize, store, and dispense liquids in a closed environment and sterile fashion, be low in cost and thus economical for disposal after a single use, and be readily adaptable as part of a continuous manufacturing process.

SUMMARY OF THE INVENTION

An object of the present invention is to provide an improved sterile fluid storage and dispensing apparatus.

Another object of the present invention is to provide an apparatus that is disposable and is particularly adapted to a process involving the manufacturing, sterilizing, and dispensing of fluids.

A further object of the present invention is to provide an improved method for manufacturing and then dispensing sterile fluids into a plurality of storage containers or elements while maintaining the sterility of the fluid.

An even further object of the present invention is to provide an improved method for mixing, filtering, sterilizing, storing, and dispensing fluids into preconnected storage and shipping containers, such method within the confines of a completely closed and sterile environment, thereby insuring against contamination.

The objects of the present invention are particularly accomplished by a bag having at least a first and second opening and made of a material that is nonreactive with the fluid; a filter element for filtering undesired elements out of the fluid prior to the fluid being placed in the bag, the filter element being located exteriorly of the bag and in communication with the first opening; a conduit element for transferring the fluid between the inside of the bag and the outside of the bag, the conduit element having one end fixed at the second opening; and a plurality of dispensing elements serially communicating with each other for providing a fluid dispensing path that can be serially opened and closed, one dispensing element being fixed at one end of the conduit element opposite the end fixed at the second opening, each dispensing element having a primary port element and an arterial port element which together provide obliquely extending port holes and further having a connecting element interfacing at least one port hole for sealably connecting the dispensing element to a receiving element or container.

The objects of the present invention are further accomplished by at least one mixing vessel for mixing the fluid, the mixing vessel being disposed in a substantially sterile environment; a reservoir container for holding the fluid transferred from the mixing vessel; at least one filling area for holding the liquid, the filling area being a communication with the reservoir container; a filter element for filtering undesired elements from the liquid prior to dispensing, the filter element being located intermediate the reservoir container and the filling area; and a plurality of storage elements interfacing the filling area, each storage element capable of being filled with liquid and then sealed off from the filling area.

These and other objects of the present invention can be seen by an examination of the attached claims, drawings, and specification.

DETAILED DESCRIPTION OF THE PRESENT INVENTION

The following description is provided to enable any person skilled in the medical and pharmaceutical fields to make and use the present invention, and sets forth the best mode contemplated by the inventor of carrying out his invention. Various modifications, however, will remain readily apparent to those skilled in these arts, since the generic principles of the present invention have been defined herein specifically to provide an improved sterile fluid storage and dispensing apparatus and improved method for filling the same.

While the present invention is described herein in the context of blood serum, artisans will understand that the present invention is not so limited. The present invention has equal application to other fluids that require preparation, sterilization, storage, and dispensing in a sterile environment.

Figure 1:
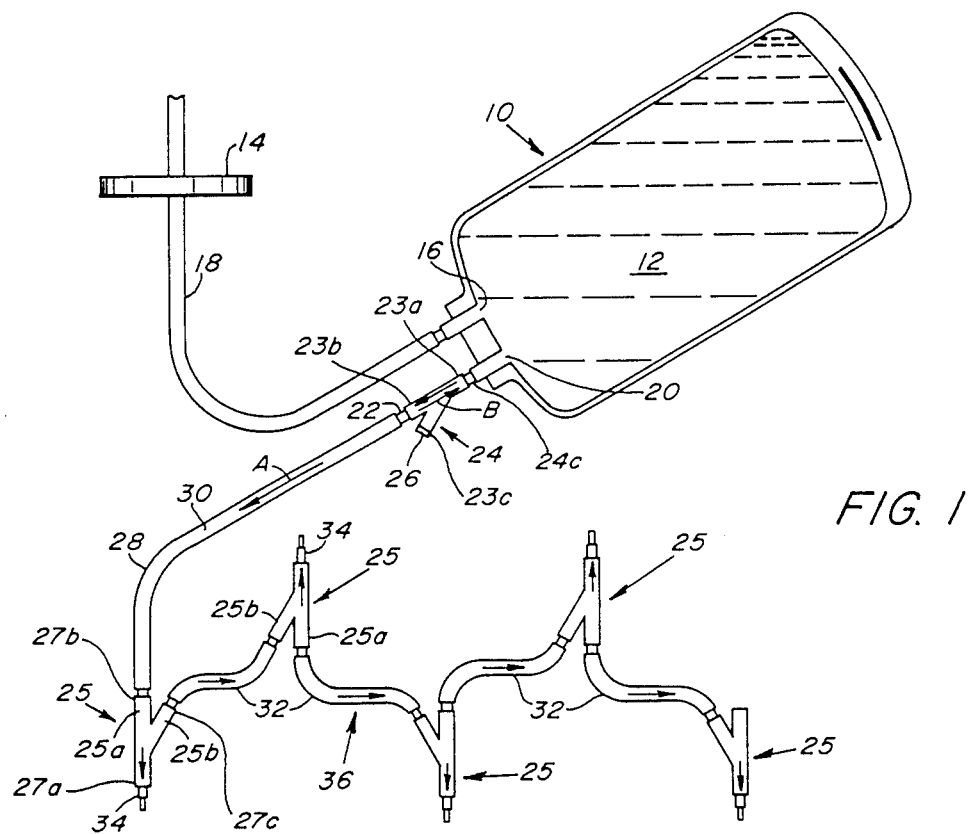
FIG. 1 is an elevated, perpective view of the storage bag of the present invention, together with a plurality of dispensing elements.

Referring to FIG. 1, a bag or storage element 10 is shown as holding blood serum or another type of sterile fluid 12. The bag 10 can be rigid but is preferably made of an appropriate flexible, polymer material known in the art which is non-reactive with the blood serum 12. See e.g., *Gajewski* et al., "Method of Storing Red Blood Cells Which Minimizes Both Red Blood Cell Hemolysis and Exposure to Blood Extractable Plasticizers," U.S. Pat. No. 4,507,387. The bag 10 is rectangular shaped and flat in its unfilled state. The bag 10 is configured to provide two circular shaped openings 16, 20 that enable the fluid 12 to pass between the inside of the bag 10 and the outside thereof. The opening 20 is configured and dimensioned like that of the opening 16 and provides a means by which the blood serum 12 can exit from the bag 10 for dispensing, as later described below. In the present embodiment, the openings 16 and 20 are on one transverse side of the bag 10. However, the present invention contemplates that the openings 16, 20 could be placed elsewhere with effectiveness. It is further contemplated that only one opening can be provided and to which a "y"—shaped connector element, like that described below, is attached with a valving mechanism to allow the fluid 12 to enter and exit the bag 10.

A conduit element 18 is joined to the opening 16 and is a flexible, elongated tube-shaped element preferably made of a polymer material that is non-reactive with the blood serum 12. The conduit element 18, in this embodiment, has an inside diameter of approximately 0.5 cm and an outside diameter slightly less than the inside diamter of the opening 16 to enable the blood serum 12 pass into the bag 10, as described below. One end of the conduit element 18 is sealed within the opening 16 in any appropriate conventional manner, such as by heat or solvent.

A filter element 14 is disposed in the fluid path way provided by the conduit element 18. The filter element 14 preferably has a plurality of pores each having a diameter of approximately 0.45 microns or less to filter out undesired elements (particularly bacteria) from the blood serum 12 prior to it entering the bag 10 from the conduit element 18. Artisans will of course understand that the size of the pores in the filter element 14 can be changed in view of the particular fluid 12 being transferred into the bag 10 and the particular types of foreign substances which the user desires to remove.

Figure 3:
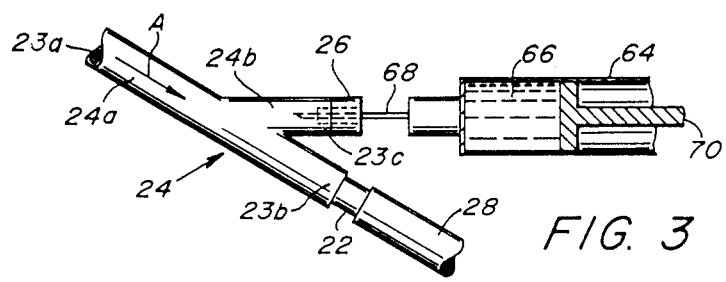
FIG. 3 is an enlarged view of a dispensing element having an injection site in which a syringe can be inserted.

A dispensing element 24 is sealably connected to the opening 20. In FIG. 3, the dispensing element 24 has a primary port element 24a and an arterial port element 24b, each of which is a generally rigid, tube-shaped element preferably made of a polymer that is non-reactive with the blood serum 12. The primary port element 24a and the arterial element 24b are joined together in a generally "y"—shaped configuration so that the arterial port element 24b extends obliquely from the straight primary port element 24a and represents one of the two top branch portions of the "y" configuration. The primary port element 24a and the arterial element 24b thereby provide three obliquely extending port holes 23a, 23b, 23c through which the blood serum 12 can pass during dispensing of the fluid 12 from the bag 10.

The port hole 23a is positioned at the end of the primary port element 24a opposite the two top branch portions of the "y" configuration. The port hole 23b is positioned at the opposite end of the primary port element 24a. The port hole 23c is positioned at the end of the arterial port element 24b opposite the end fixed to the primary port element 24a. A tube-shaped element 24c extends from the primary port element 24a at the port hole 23a and has an outside diameter slightly less than the inside diameter of the primary port element 24a. The element 24c is inserted into the opening 20 and provides a means by which the dispensing element 24 can be sealably fixed to such opening, as by heat sealing.

A seal element 26 is sealably fixed about the port hole 23b and serves as an injection site as described hereinafter. The seal element 26 is preferably made of a pliable, polymer material having a cup like configuration that sealably fits about the distal end of the arterial port element 24b. The seal element 26 further includes a hollowed post element that extends from the base of the cup configuration and into the port hole 23c. The seal element 26 thereby provides an injection site for insertion of a needle 68 from a syringe 64, as seen in FIG. 3. The syringe 64 may contain a reagent 66, such as an anticoagulent, that might be required to be added to the blood serum 12 prior to dispensing in the manner described hereinafter. A plunger 70 in the syringe 64 can be depressed to displace the reagent 66 through the needle 68 and into the dispensing element 24. As the fluid 12 moves in a direction A (FIG. 1) through the dispensing element 24, the reagent 66 will be drawn into the stream of the fluid 12 for subsequent dispensing.

A valve element 22 may be provided to interface the port hole 23b. The valve element 22 is of any appropriate design known in the art to provide a one way valving mechanism so that the fluid 12 is allowed to pass out of the dispensing element 24 only in the direction A, and not back into the dispensing element 24 in a direction B (FIG. 1).

Figure 2:
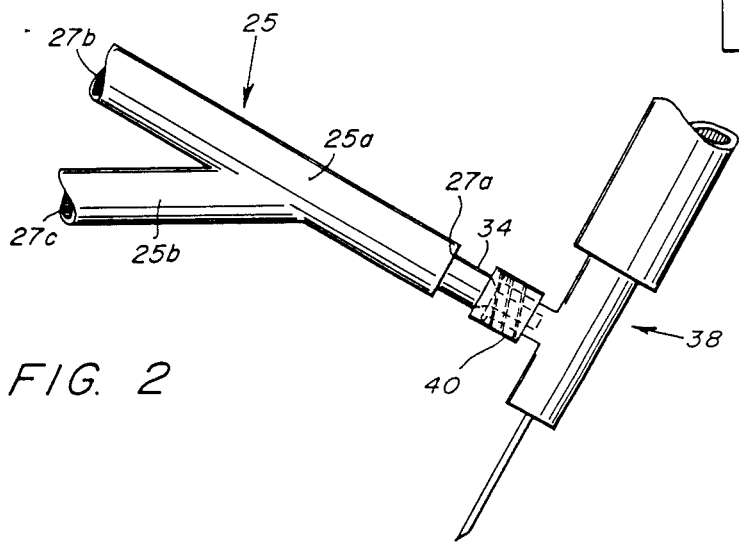
FIG. 2 is an enlarged view of a dispensing element connected to a syringe.

As the fluid 12 passes through the valve element 22, the fluid 12 enters into an enlongated, flexible conduit element 28 which is configured and dimensioned like that of the conduit element 18. The conduit element 28 has one end sealably fixed to the valve element 22 at the port hole 23b and provides a fluid transfer path 30 through which the fluid 12 can pass until it reaches the first of a series of dispensing elements 25. The end of the conduit element 28 opposite the end fixed to the valve element 22 is sealably connected to a dispensing element 25, which is configured and dimensioned like that of the dispensing element 24. The dispensing element 25 has a primary port element 24a and an arterial port element 24b which obliquely extends from the former in a generally "y"—shaped configuration and provides three obliquely extending port holes 27a, 27b, 27c (FIG. 2).

The port holes 27a,b,c are disposed at the ends of the primary port element 24a and the arterial port element 25b in a fashion like the port holes 23a,b,c vis-a-vis the dispensing element 24. Thereby, the port hole 27b interfaces the end of the conduit element 28 opposite the dispensing element 24. The port hole 27a interfaces a connector element 34.

The connector element 34 is a preferably a male type element, such as that in a luer lock mechanism well known in the medical field. As shown in FIG. 2, the connector element 34 can connect to a connector element 40, such as a female type connector in a luer lock mechanism. In FIG. 2, the female connector element 40 is shown in the context of a cornwal-type syringe 38 which acts as a receiving element or container for the blood serum 12.

A conduit element 32 is provided and has a configuration and dimension similar to that of the conduit element 28. The conduit element 32 has one end sealably connected to of the first dispensing element 25 in the series at its port hole 27c (FIG. 1). The other end of the conduit element 32 is sealably connected to a second dispensing element 25 at its arterial port element 25b. As shown in FIG. 1, there is a series of five dispensing elements 25 joined together by four conduit elements 32. The series of dispensing elements 25 and conduit elements 32 provide a fluid dispensing path 36 which can be serially opened and then closed in the manner described hereinafter. When a dispensing element 25 is not being used, the connector element 34 remains protected from exterior environment contaminants by a cap member (not shown) commonly used to close luer locks. As can be appreciated, the number of dispensing elements 25 and the number of conduit elements 32 can be modified as needed for the particular circumstances. Further, in this particular embodiment, the dispensing elements 25 are shown in FIG. 1 as oppositely facing and alternating. However, other arrangements of the dispensing elements 25 are contemplated.

Figure 4:
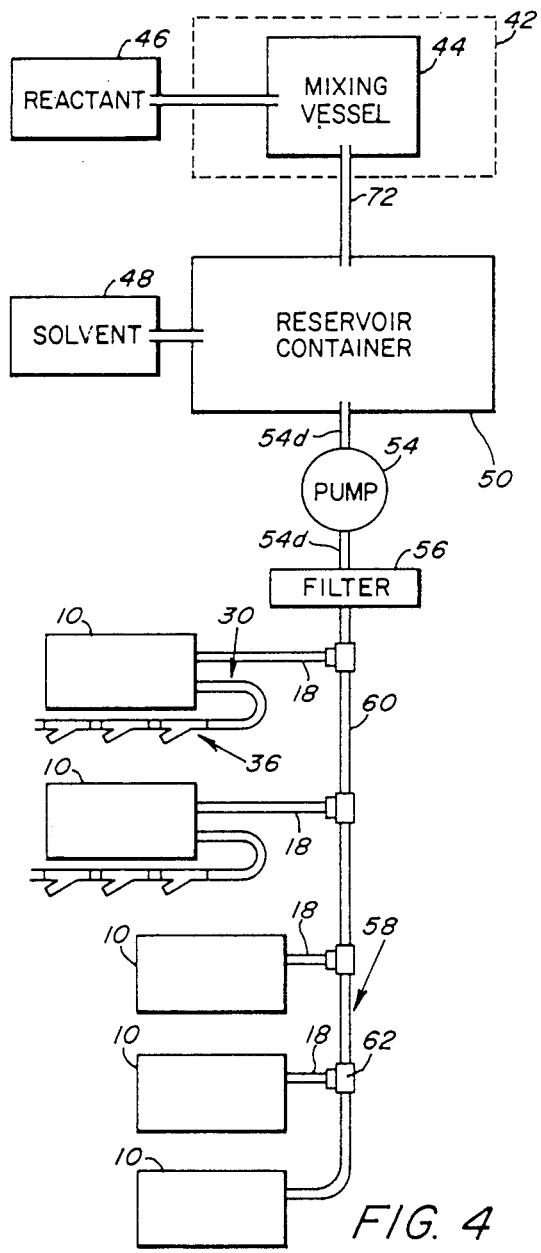
FIG. 4 is a diagrammatical view of an assembly of the present invention for mixing, sterilizing, and then dispensing a fluid into a plurality of pre-connected storage bags.
Figure 5:
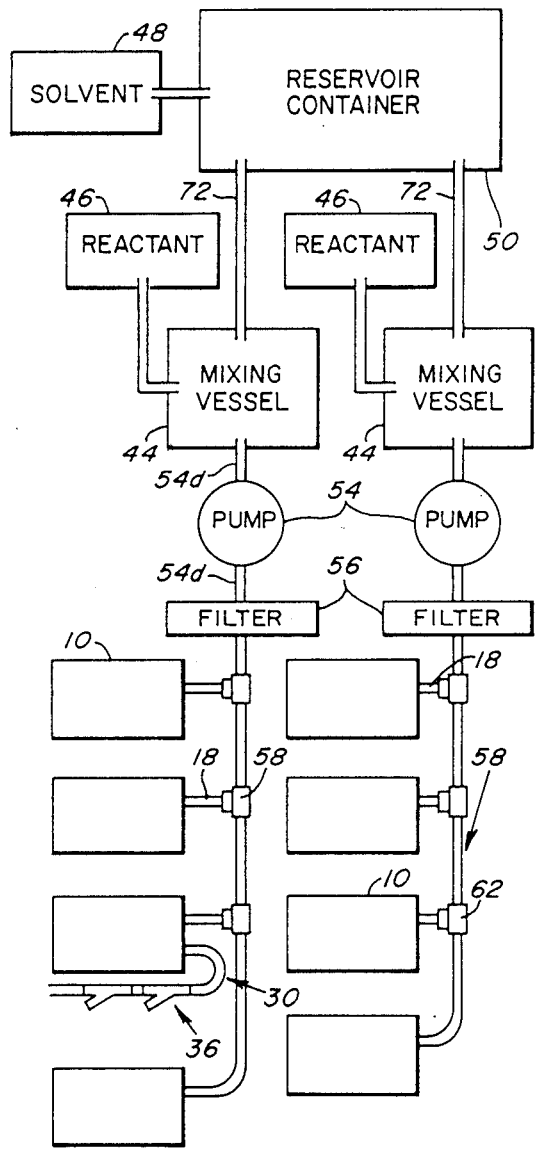
FIG. 5 is another embodiment of the present invention for mixing and then dispensing the fluid into a plurality of storage bags.

The apparatus shown in FIG. 1 is preferably sterilized prior to use, such as by gamma radiation, and can be incorporated into a larger assembly for mixing the fluid 12 and subsequent dispensing into a plurality of bags 10, as shown in FIGS. 4 and 5 which represent two different embodiments of the present invention. In FIG. 4, a mixing vessel 44 is provided for mixing the fluid and is made of an appropriate material that is non-reactive with the fluid 12 and can be sterilized, such as with solvents or gamma radiation. Preferably, the mixing vessel 44 is made of a flexible polymer material, like bag 10, and is disposed of after being used only once. A source of reactants 46, preferably in solid form, is provided for introduction into the mixing vessel 44. The mixing vessel 44 is maintained in a sterile or clean environment 42, such as in a sterile hood that provides an air flow therein to remove bacteria that would otherwise increase the bacterial count in the fluid 12. The mixing vessel 44 in this embodiment has a volumetric capacity of approximately 30 liters.

A reservoir container 50 is provided and has, in this embodiment, a volumetric capacity of approximately 1,000 liters. Other volumetric capacities could, of course, be desireable. The reservoir container 50 is made of a material like that of mixing vessel 44, and remains readily disposable following a single mixing and dispensing in the manner described below. The reservoir container 50 is preferably sterilized, like the mixing vessel 44, prior to use and provides a closed, sterile environment with an opening to the mixing vessel 44.

The closed environment of the reservoir container 50 remains in liquid communication with the mixing vessel 44, through a pre-sterilized disposable conduit element 72, but outside of the clean environment 42. In addition, a solvent source 48 remains in liquid communication with the closed environment of the reservoir container 50. Thereby, the solvent 48 in the reservoir container 50 can be introduced into the mixing vessel 44, such as by pumping forces or gravitational forces. The reactant 46 and the solvent 48 are then mixed in the mixing vessel 44 and transferred back into the closed environment of the reservoir container 50.

Figure 6:
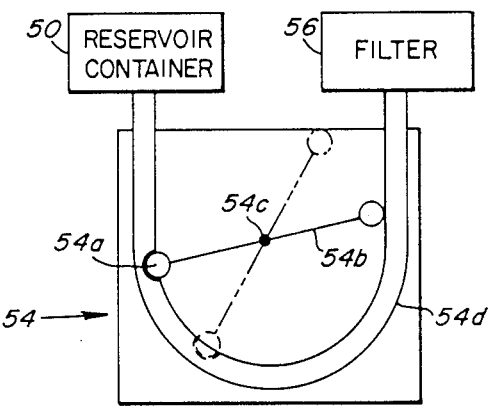
FIG. 6 is a partial view of the pump used in connection with the assembly shown in FIGS. 4 and 5.

A pump 54, being of any appropriate conventional peristaltic design, is provided to pump the fluid 12 out of the reservoir container 50 and through the filter element 56. The pump 54 is preferably the Varistaltic Pump Series A made by Manostat of New York, N.Y. (FIG. 6) and has a pair of roller elements 54a held by a pair of arm elements 54b. The arm elements 54b rotate about an axis 54c and cause one of the roller elements 54a to provide a rolling force against a tube 54d that carries the fluid 12 between the reservoir 50 and the filter 56. The tube 54d is preferably a silastic tubing by Dow-Corning and is disposed of after a single mixing and dispensing of the fluid 12.

The filter element 56 is also of any appropriate conventional design and includes a plurality of pores whose diameters can vary depending upon the elements desired to be removed from the fluid 12. In the context of sterilizing blood serum, the pores are approximately 0.22 microns or less.

A conduit element 60 is provided and has one end sealably fixed to the filter element 56 at a point that can receive the fluid 12 after it has been filtered. The conduit element 60 is preferably a flexible, polymer element having an inside diameter approximately twice that of the conduit element 18. A plurality of connector elements 62 are serially interposed along the conduit element 60. Each connector element 62 is a generally rigid, tube shaped element in a "T"-shaped configuration that provides three port holes. The portion of the connector element 62 that extends horizontally across the top of the element is sealably connected to the conduit element 60. The vertically aligned portion of the connector element 62 is sealably connected to the conduit element 18 as shown in FIG. 4. The conduit element 60 and the plurality of connector elements 62 provide a closed, sterile environment or filling area 58 through which the fluid 12 can pass for dispensing into a plurality of pre-connected bags 10. Again, prior to use, the tube 54d, the filter element 56, the conduit element 60, and the connector elements 62 are sterilized prior to use. After a single use, all of those elements can be disposed.

In FIG. 5, two or more mixing vessels 44 can be provided in connection with a single reservoir container 50. After the fluid 12 is mixed in the mixing vessels 44, the fluid 12 is transferred out of each of the mixing vessels 44 and through the filter elements 56 and into the filling areas 58 for dispensing into the bags 10. In this embodiment, different reactants 46 can be associated with respective mixing vessels 44 to enable different fluids 12 to be manufactured.

As can be appreciated, the assemblies in FIGS. 4 and 5 provide a closed environment in which the fluid 12 is mixed, sterilized, and dispensed, and also provides a disposable apparatus for filling a plurality of bags 10 or other receiving elements in a sterile fashion. In the context of FIG. 4, the reactant 46 and the solvent 48 are mixed in the mixing vessel 44 which is within the clean environment 42. The mixed fluid 12 then passes into the reservoir container 50 and is then pumped out of the same by the pump 54 and through the filter element 56. After passing through the filter 56, the fluid 12 is substantially sterile and free of bacteria. The fluid 12 then enters into the filling area 58 and moves through the conduit elements 18 associated with each of the bags 10. When each of the bags 20 is filled with the fluid 12, the bags 10 are then sterilely removed from the filling area 58, such as by heat sealing each of the respective conduit elements 18. This maintains the integrity of the closed system.

The user is then provided with a plurality of storage and dispensing assemblies as shown in FIG. 1. When the user desires to extract a portion of the fluid 12 from the bag 10, the dispensing element 25 which is disposed farthest from the opening 20 can be opened through the connector element 34 and attached to a respective connector element 40 of a receiving element such as a cornwal syringe 38. After the receiving element is filled, the connector elements 34, 40 are disengaged, and the conduit element 32 intermediate the farthest removed and next farthest removed connector elements 25 is sealed, such as by heat. When further dispensing from the bag 10 is required, the user then opens the dispensing element 25 which is the next farthest removed from the opening 20 in the bag 10. A process similar to that of the first dispensing element 25 is then carried on. This procedure can continue until all of the fluid 12 is dispensed. In such a fashion, each dispensing element 25 is opened only once and the system provided by the present invention remains substantially free of undesired elements.

As can be appreciated, after the bags 10 have been filled, the filling area 58 can be sealed off from the filter 56, such as by heat. Then the mixing vessel 44, the conduit element 72, the reservoir container 50, the tube 54d, and the filter 56 are not reused but instead thrown away to maintain sterility. Similarly, after the fluid 12 that has been dispensed from the bags 10, the bags can be thrown away.

It is understood, of course, that the foregoing description relates only to preferred embodiments of the present invention and that modifications thereto may nevertheless come within the scope of the invention.

What is claimed is:

1. A disposable assembly for mixing, sterilizing, storing, and dispensing fluids, all of which occur in a closed and sterile environment, comprising:

at least one disposable mixing vessel for mixing the fluid, the mixing vessel being disposed in a substantially sterile environment;
   a disposable reservoir container for holding the fluid transferred from the mixing vessel;
   at least one disposable filling area for holding the liquid, the filling area being in communication with the reservoir container and also having been sterilized and placed in communication with the reservoir container prior to sterilizing and storing the fluid;
   a sterilizing means for sterilizing the liquid prior to storing, the sterilizing means being located intermediate of and in communication with the reservoir container and the filling area, the sterilizing means also having been sterilized and placed in communication with the filling area prior to sterilizing and storing the fluid; and
   at least one storage element in communication with the filling area, the storage element having been sterilized and placed in communication with the filling area prior to sterilizing the fluid, and capable of being filled with the liquid and then sealed off from the filling area, whereby a sterile environment is formed by the filling area, the sterilizing means, and the storage element prior to sterilizing the fluid, and said environment remains sterile while the fluid is being sterilized and while the storage element is being filled.

2. The invention of claim 1 wherein the volumetric capacity of the reservoir container is substantially greater than that of the mixing vessel.

3. The invention of claim 1 wherein each storage element is serially aligned along the filling area.

4. In an assembly for mixing a fluid, transferring the fluid out of a container, and then processing the fluid into at least one receiving element, a disposable apparatus for sterilizing, storing, and dispensing the fluid, comprising:

a sterile environment that remains continuously closed to the entrance of undesired elements outside of the environment and which has been formed prior to transferring the fluid out of the container, the environment being affixed to the container and having:
   a conduit means for transferring the fluid along a longitudinally extending filling area having one end interfacing the container, the conduit means having at least one first connector element sealed along the filling area, the conduit means also having been sterilized prior to sterilizing the fluid;
   a sterilizing means for sterilizing the fluid, the sterilizing means disposed within the filling area at the end immediately interfacing the container, the sterilizing means also having been sterilized prior to the fluid being sterilized; and
   at least one storage element that is sealed to a respective first connector element to remain in fluid communication with the filling area, each storage element also having been sterilized prior to sterilizing the fluid, whereby the conduit means, the sterilizing means, and the storage element have been connected to one another and then sterilized to form the environment prior to sterilizing the fluid.

5. The invention of claim 4 wherein each storage element is serially disposed along the filling area.

6. A method for manufacturing, sterilizing, and dispensing fluids within a closed environment, comprising the steps of:

preparing the fluid in a disposable mixing vessel which is located in a substantially sterile environment;

transferring the fluid from the mixing vessel to a disposable reservoir container;

placing at least one disposable storage element in communication with a disposable liquid filling area which is in communication with the reservoir container;

placing a disposable sterilizing element intermediate of and in communication with the reservoir container and the filling area;

sterilizing the storage element, the sterilizing element, and the filling area as a single entity after they have all been placed in communication with each other;

moving the fluid from the reservoir container through the disposable sterilizing element and into the liquid filling area after the sterilizing element, storage element, and the filling area have been sterilized;

filling the storage element with the prepared fluid from the filling area; and sealing off the storage element from the liquid filling area to permit the storage element to be disconnected from the liquid filling area while leaving the liquid filling area sealed, whereby the steps of moving the fluid through the sterilizing element and into the filling area, and then filling the storage element occur within a continuously closed and sterile environment.

7. the invention of claim 6 wherein the step of sterilizing the storage element, the filter element, and the liquid filling area occurs prior to the step of moving the fluid into the liquid filling area.

8. The invention of claim 7 wherein the step of placing the storage elements in communication with the liquid filling area includes the step of serially sealably connecting the storage elements to the filling area.

9. The invention of claim 1 wherein the mixing vessel has been sterilized prior to mixing the fluid.

10. The invention of claim 9 wherein the reservoir container has been sterilized prior to mixing the fluid.

11. The invention of claim 1 further including at least one dispensing element fixed to the storage element.

* * * * *

UNITED STATES PATENT AND TRADEMARK OFFICE
CERTIFICATE OF CORRECTION

PATENT NO. : 4,754,786

DATED : July 5, 1988

INVENTOR(S) : Roderick Roberts

It is certified that error appears in the above-identified patent and that said Letters Patent is hereby corrected as shown below:

Column 1, line 66, delete "a" and insert --an--therefor;

Column 3, line 62, delete "diamter" and insert --diameter-- therefor;

Column 5, line 8, delete "24a" and insert --25a-- therefor;

Column 5, line 9, delete "24b" and insert --25b-- therefor;

Column 5, line 13, delete "24a" and insert --25a-- therefor;

Column 5, line 19, delete "a" (first occurrence);

Column 7, line 22, delete "20" and insert --10--therefor.

Signed and Sealed this

Sixteenth Day of May, 1989

Attest:

DONALD J. QUIGG

Attesting Officer

Commissioner of Patents and Trademarks